United States Patent [19]

Braverman

[11] Patent Number: 4,517,388

[45] Date of Patent: May 14, 1985

[54] PROCESS FOR THE SELECTIVE PREPARATION OF PARABROMOPHENOL AND ITS DERIVATIVES

[76] Inventor: Samuel Braverman, 65/26 Harey-Yehuda St., Ganei Tiqva 55900, Israel

[21] Appl. No.: 545,212

[22] Filed: Oct. 25, 1983

[30] Foreign Application Priority Data

Oct. 29, 1982 [IL] Israel .................................. 67117

[51] Int. Cl.$^3$ .............................................. C07C 39/27
[52] U.S. Cl. .................................... 568/779; 568/774
[58] Field of Search ................................ 568/779, 774

[56] References Cited

U.S. PATENT DOCUMENTS

| | | | |
|---|---|---|---|
| 2,805,263 | 9/1957 | Kaeding et al. | 568/779 |
| 3,546,302 | 12/1970 | Asadorian et al. | 568/779 |
| 3,920,757 | 11/1975 | Watson | 568/779 |
| 4,210,766 | 7/1980 | Somlo | 568/779 |

Primary Examiner—Werren B. Lone

[57] ABSTRACT

This invention is a process for the preparation of para-bromo-phenole derivatives of the formula I

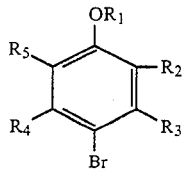

wherein $R_1$, $R_2$, $R_3$, $R_4$ and $R_5$ each independently represents hydrogen or lower alkyl radical of 1 to 6 carbon atoms, characterized in that a phenol derivative of formula II

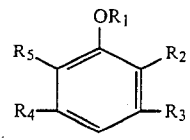

wherein $R_1$, $R_2$, $R_3$, $R_4$ and $R_5$ are as defined above, is reacted in the presence of a solvent with a compound of the formula

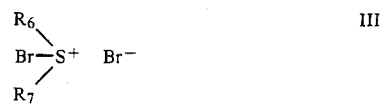

or with bromine and a compound of the formula IV

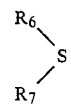

wherein $R_6$ and $R_7$ in the formulae III and IV being each independently a lower alkyl radical of 1 to 6 carbon atoms, an aryl radical or they form together with the S-atom to which they are attached, a 4 to 6 member ring.

7 Claims, No Drawings

PROCESS FOR THE SELECTIVE PREPARATION OF PARABROMOPHENOL AND ITS DERIVATIVES

The present invention relates to a new process for the preparation of para-bromophenol and para-bromophenol derivatives.

Para-bromophenol and its derivatives are useful commercial materials. Thus, some of them serve as disinfectants and others as fungicides and bactericides or as intermediates in the preparation of pharmaceutical and agricultural chemicals.

The preparation of para-bromophenol and its derivatives, like the preparation of other para-substituted compounds, presents many difficulties due to the non-selectivity of the bromo-substitution on the benzene ring. It is common that substitution in a benzenoid compound which contains an ortho- and para-directing substituent gives comparable proportions of the ortho- and para-derivative, so that the maximum yield of the para-derivative is only about 50%. Furthermore, these two derivatives may have similar physical properties to the extent that separation is tedious and results in losses. Highly activated nuclei such as phenols and cresols present a further difficulty, and it is sometimes impossible even under mild conditions to arrest an ongoing bromination before all the strongly activated positions have been substituted. Thus, as indicated in "Bromine and its compounds" by C. T. Pumpelly, Z. E. Jolles (Ed) Ernest Benn, London, 1966, p. 71, phenol gives 2,4,6-tribromophenol essentially instantaneously when treated with bromine or an aqueous solution thereof.

Attempts have already been made to overcome these difficulties. Thus, processes for the preparation of para-bromophenol and para-bromoanisole are described in the literature which yield the para-compound in preference, but all these known processes suffer from disadvantages which render them impractical for industrial application. Among the disadvantages of the known processes there may be mentioned safety problems due to the use of highly inflammable or toxic solvents; the need to operate at either very low or very high temperatures; the use of uncommon complex brominating agents; and low yields.

Adams and Marvel in Org. Syn. Coll., Vol. I, 128 (1941) described the bromination of phenol with bromine in carbon disulfide as solvent at a temperature below 5° C. The yield of para-bromophenol was 80–84%, and the product had to be isolated and separated from the o-isomer by the use of fractional distillation at reduced pressure. In order to try and overcome the problems arising from the use of highly inflammable and toxic $CS_2$, the use of carbon tetrachloride was examined. However, since the solubility of the phenol in carbon tetrachloride is much lower at the reaction temperature, much larger quantities of solvent were required. Also, the removal of solvent was more difficult and the proportion of o-bromophenol obtained was slightly greater compared with the same process in $CS_2$.

Podall and Foster in J. Org. Chem., 23, 280(1958), describe bromination in ethylene dichloride as solvent at 0° C. using a 20% or larger excess of phenol. The excess phenol and the ortho-bromophenol obtained as by-product were removed by fractional distillation at reduced pressure. The yeild of para-bromophenol obtained was 93%, and 98% pure based on infrared spectrum analysis. The need to operate at the low temperature of 0° C. and to use superfluous amounts of phenol which later on must be removed, are obviously the major disadvantage of the above process.

U.S. Pat. No. 2,452,154 discloses the preparation of para-bromophenol in 91.5% yield by reacting bromine with phenol at −8° C., in liquid sulfur dioxide. Thus, though the product is obtained in relatively high yield, the need to carry out the reaction under the low temperature of −8° C. imposes a major disadvantage on the above process.

U.S. Pat. No. 2,805,263 discloses the halogenation of phenol with copper(II) chloride as well as with copper(II) bromide. When the reaction was carried out in water at 275° C., the relative yield of the para derivative is 20%, while under anhydrous conditions at 180° C., the yield is about 50%.

Kosower and co-workers in J. Org. Chem. 28, 630 (1963), reported that the bromination of phenol with copper (II) bromide in dimethylformamide at 100° C. for two hours produced a mixture of mono-bromophenols with a para/ortho ratio of about 11:1, together with 2,4- and 2,6-dibromo- and 2,4,6-tribromophenol. The relative yield of para-bromophenol under this condition was reported to be 67%, the recovery 60% and the conversion 75%, thus the yield of para-bromophenol over the phenol was only 30%.

Chem. Abst. 75,35302a (1971) discloses a selective method for mono-bromination of phenol and phenol derivatives, i.e. ortho- and para-cresol or anisole, with 2,4,4,6-tetrabromocyclohexa-2,5-dienone. When the reaction was carried out for phenol in $CCl_4$ a 95% mixture of ortho- and para-bromophenol in the ratio of 9.0 was obtained. When acetonitrile was used as solvent the ratio was 0.04. However, though the yields of para-bromophenol when acetonitrile was used as solvent, were high the above process is impractical for industrial applications due to the complexity and high costs of the brominating agent employed.

An indirect and therefore complicated method for the preparation of para-bromophenol has also been described by Hoffman et al in Ber. 95,523 (1962). Triphenyl phosphine was used for the preferential reductive displacement of an ortho bromine atom from 2,4-dibromophenol. The reaction was performed in a sealed tube at 100°–150° for 1–5 hours, using benzene as a solvent.

Chem. Abst. 47,8032 (1953) discloses the use of dioxane dibromide in the preparation of para-bromophenol. The brominating reagent is added with cooling to a solution of phenol in anhydrous ether. Evaporation of the ether followed by fractional distillation at low temperature gives para-bromophenol in 90% yield. Though relatively high yields of the desired product were obtained, the industrial usefulness of the process is limited due to the high volatility of the brominating agent and the need to operate at low temperatures.

Most of the known methods for the selective preparation of p-bromophenol and its derivatives have not become commercial due to their many disadvantages as pointed out above. Thus, it is the object of the present invention to provide a new, simple, low cost process for the selective para-bromination of phenol and its derivatives.

In accordance with the present invention there is provided a process for the preparation of para-bromophenol derivatives of formula I

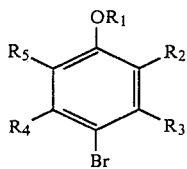

wherein $R_1$, $R_2$, $R_3$, $R_4$ and $R_5$ each independently represent hydrogen or lower alkyl radical of 1 to 6 carbon atoms, characterized in that a phenol derivative of formula II

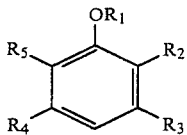

wherein $R_1$, $R_2$, $R_3$, $R_4$ and $R_5$ are as defined above, is reacted in the presence of a solvent with a compound of the formula

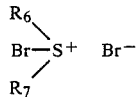

or with bromine and a compound of the formula

wherein $R_6$ and $R_7$ in formulae III and IV being each independently a lower alkyl radical of 1 to 6 carbon atoms, an aryl radical or they form together with the S-atom to which they are attached, a 4 to 6 membered ring.

The yields of the para-bromophenol and its derivatives in the process according to the invention are very high and usually range between 95-100%. In some cases, lower yields of the desired product ranging between 85-95% are obtained. However, those cases present other advantages as shown below.

The temperature of the reaction is not critical and may vary within a wide range. In many cases the temperature range of 20°-30° C. is suitable.

The process according to the invention does not present any special requirement as regards the solvent, and a wide range of solvents including the most common, inexpensive and safe organic solvents can be used. A further advantage of the process under the invention is the employment of a simple and easy to prepare brominating agent.

The brominating agent according to the present invention is a sulfonium bromide salt as defined by formula (III) or bromine together with a sulfide as defined by formula (IV). Sulfonium bromide salts in general and bromo-dimethylsulfonium bromide (BDMSB) in particular can be easily prepared as described, for example by G. A. Olah et al in Synthesis 720 (1979) or by A. H. Fenselau and J. G. Moffat in J. Amer. Chem. Soc. 88,1762 (1966), by treatment of dimethyl sulfide with bromine in either carbon tetrachloride or in methylene chloride at 0° C. N. Furukawa et al in J.C.S. Chem. Comm., 212 (1973) reported that BDMSB reacts with various aliphatic alcohols, used in excess, at about 80° for 4-5 hours, to give the corresponding alkyl bromides. For primary alcohols the yields were good (about 75%) while for secondary and tertiary alcohols the yields were considerably lower. However nowhere in the literature has it been disclosed or suggested that BDMSB could be a selective brominating agent for the preparation of para-bromophenol or its derivatives.

The process in accordance with one embodiment of the invention can be depicted by the following chemical equation:

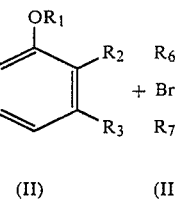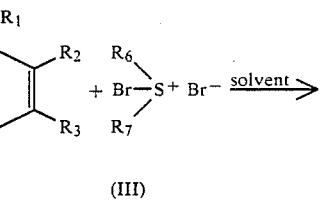

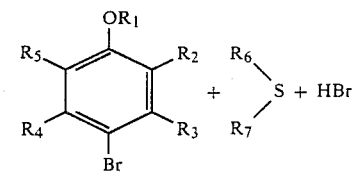

wherein $R_1$, $R_2$, $R_3$, $R_4$, $R_5$, $R_6$ and $R_7$ are as defined above. Thus, equimolar quantities of phenol derivatives and brominating agent produce the same molar quantity of product. The gaseous HBr liberated in the course of the reaction can be trapped and used for other purposes. The sulfide formed as a by-product and the solvent are removed by evaporation and the said bromination product remains as residue. The sulfide, if desired, can be recycled, e.g. for the production of a compound of formula (III). Yields of the desired product in accordance with the above embodiment are very close to 100%.

Alternatively the brominating agent can be prepared in situ. Thus, in accordance with another embodiment of the invention (hereinafter referred to as the "Direct Method"), the sulfide of formula (IV) and bromine are mixed at the desired molar ratio in a suitable solvent and immediately thereafter a compound of formula II is added. After the reaction is terminated the solvent and the sulfide are evaporated and the bromination product remains as residue. The sulfide may be recycled, back to the reaction. The yield of the desired product in accordance with the Direct Method is very close to 100%.

A further embodiment of the invention (hereinafter referred to as the "Catalytic Method") enables to carry out the selective bromination reaction using considerably smaller amounts of the sulfide as compared with the stoichiometric amount thereof usually needed in the Direct Method. In accordance with this embodiment the required amount of bromine is added gradually to a solution of the compound of formula II in the presence of a catalytically effective amount of the sufide which may be as low as one hundredth of the stoichiometric amount. It is believed that in accordance with this procedure the sulfide reacts with the bromine to form the sulfonium bromide which selectively brominates the phenol or phenol derivative in the paraposition, releasing the sulfide, which again reacts with bromine to form the sulfonium bromide etc., and in this way the sulfonium bromide is continually regenerated by the fresh amounts of bromine added.

Yields according to the catalytic methods are relatively lower than in the other two methods described above, ranging between 84 and 95%. However, since the amount of sulfide employed in accordance with this method is significantly lower, thus, the man of the art who wishes to utilize the invention for industrial application should weigh and balance his requirements for selectivity of the process against his requirements for simplicity of operation and choose among the different modifications of the process according to the invention.

The reaction according to the Direct Method and the Catalytic Method is depicted by the following chemical equation:

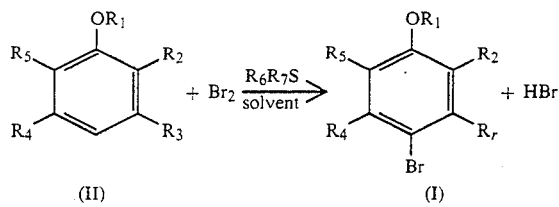

wherein $R_1$, $R_2$, $R_3$, $R_4$, $R_5$, $R_6$ and $R_7$ are as defined above.

The solvent in accordance with the present invention may be any organic solvent capable of dissolving the reactants and being inert to bromine. When carrying out the reaction at room temperature a solvent of high volatility, such as methylene chloride, is preferred.

The preferred compounds of formula I in accordance with the present invention are para-bromophenol, para-bromoanisole and 4-bromo-2-methylphenol.

A preferred brominating reagent used in accordance with the invention is bromo-dimethylsulfonium bromide (BDMSB) or a mixture of bromide with either dimethylsulfide or diethylsulfide.

The invention is illustrated by the following non-limiting Examples.

EXAMPLE 1

Preparation of para-bromophenol using BDMSB (a) Preparation of BDMSB

The BDMSB reagent was prepared according to the procedure described by Olah and co-workers in Synthesis, 720 (1979). Thus, a solution of bromine (40 g, 0.025 mole) in 50 ml of dry methylene chloride was added dropwise over approx. 30 min. to a solution of dimethylsulfide (15.5 g, 0.25 mole) in 50 ml of dry methylene chloride with stirring and cooling in an ice-water bath. The heavy precipitate of light orange crystalline BDMSB was separated by filtration and dried under vacuum overnight. Yield 51.5 g (92%).

(b) Preparation of p-bromophenol

In an 100 ml round bottom flask equipped with a magnetic stirrer, were placed 2.220 g (10 mmoles) of bromodimethylsulfonium bromide, immediately followed by the addition of 15 ml of dry methylene chloride. A solution of phenol (0.940 g, 10 mmoles) in 10 ml of dry methylene chloride was then added dropwise by means of a pressure equalizing separatory funnel during appx 20 min, with stirring at room temperature. The reaction of phenol with BDMSB appears to be instantaneous as indicated by the complete disappearance of the solid reagent, if all the phenol is added at once. Evaporation of the solvent (bp, 40°) and the reaction by-products, dimethyl sulfide (bp, 38°) and gaseous HBr, with the aid of a rotavapor left the expected product in practically quantitative yield (95–100%). To remove traces of HBr it is advisable to redissolve the residue, treat with $CaCO_3$, filter and remove the methylene chloride again. The NMR spectrum displayed a singlet at δ 5.8 (1H) due to the hydroxylic proton, and an aromatic AA'BB' quartet (4H) centered at δ 6.9 (Δυ=0.6 ppm, $J_{AA'}=J_{BB'}=8$ Hz). This spectrum is practically identical with the spectrum of a sample of p-bromophenol produced by Fluka AG as well as with the spectrum published in the Aldrich Library of NMR Spectra, Vol. 4, p. 116. The purity of the compound was determined by gas chromatographic analysis which gave the following results: 97.2% p-bromophenol, 2.1% o-bromophenol, 0.5%–2,4-dibromophenol, 0% phenol.

EXAMPLE 2

Preparation of p-bromophenol by the "Direct Method"

In a 250 ml round bottom flask were placed 1.4 g (23 mmoles) of dimethyl sulfide and immediately dissolved with 20 ml of dry methylene dichloride. After cooling in an ice-water bath, a solution of 3.2 g (20 mmoles) of bromine in 20 ml of dry methylene chloride was added dropwise with magnetic stirring over 10 mins. Next, 1.8 g (19 mmoles) of phenol dissolved in 16 ml of dry methylene chloride was added dropwise over a few mins, and stirring was continued for another two and a half hours. Evaporation of the solvent followed by treatment with $CaCO_3$ to remove traces of HBr, gave 3.5 g (103%) of product which had an NMR spectrum practically identical with that of p-bromophenol, as indicated in Example 1.

EXAMPLE 3

Preparation of para-bromophenol by the "Catalytic Method"

To a solution of phenol (10 mmoles) in 10 ml of methylene chloride, in the presence of 1 molar percent of diethyl sulfide (1 ml of 0.1M sol of the sulfide in $CCl_4$), was added dropwise a solution of bromine (10 mmoles) in 10 ml of the same solvent, at a rate determined by the disappearance of the bromine colour (a few minutes). Evaporation of the solvent and neutralization over $CaCO_3$ gave a product that gas chromatographically analyzed as follows: 84.3% p-bromophenol, 6.8% o-bromophenol and 8.9% phenol.

The same experiment was repeated with carbon tetrachloride as solvent. By gas chromatographic analysis the product consisted of 87.5% p-bromophenol, 8.7% o-bromophenol and 3.8% phenol.

EXAMPLE 4

Preparation of 4-bromo-2-methyl phenol

Ortho-cresol was brominated with BDMSB, as described for the bromination of phenol in Example 1. The product gave a yield of 91% and gas chromatographic analysis showed 90% of 4-bromo-2-methyl phenol, 5% of 6-bromo-2-methyl phenol and 5% of starting material.

EXAMPLE 5

Preparation of p-bromoanisole

Para-anisole was brominated with BDMSB as described for the bromination of phenol in Example 1, except that the reaction time was three hours. Yield 102%; NMR spectrum identical with the p-bromoanisole spectrum published in Aldrich Library of NMR Spectra, Vol. 4, p. 89.

EXAMPLE 6

Preparation of p-bromoanisole by the "Catalytic Method"

Para-anisole was brominated as described for the bromination of phenol in Example 3. Yield 95%; NMR spectrum as mentioned in Example 5.

I claim:

1. A process for the preparation of para-bromophenol derivatives of formula I

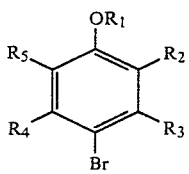

wherein $R_1$, $R_2$, $R_3$, $R_4$, and $R_5$ each independently represent hydrogen or lower alkyl radical of 1 to 6 carbon atoms, characterized in that a phenol derivative of formula II

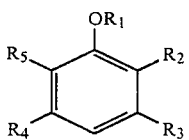

wherein $R_1$, $R_2$, $R_3$, $R_4$ and $R_5$ are as defined above is reacted preferably at a temperature of between 20° and 30° C., in the presence of a solvent with a compound of the formula

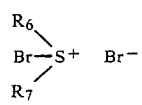

or with bromine and a compound of the formula

wherein $R_6$ and $R_7$ in formulae III and IV being each independently a lower alkyl radical of 1 to 6 carbon atoms, an aryl radical or they form together with the S-atom to which they are attached a 4 to 6 membered ring.

2. A process according to claim 1, wherein a compound of formula II is reacted with a ready-made compound of formula III.

3. A process according to claim 1, wherein a compound of formula III is produced in situ by first mixing bromine and a compound of formula IV, at the desired molar ratio in the presence of a solvent, and a compound of formula II is then added.

4. A process according to claim 1, wherein bromine is reacted with a compound of formula II in the presence of a catalytically effective amount of a compound of formula IV.

5. A process according to any one of claims 1 to 4, wherein $R_6$ and $R_7$ in the compounds of formulae III and IV are methyl or ethyl groups.

6. A process according to any one of claims 1 to 5, wherein the compound of formula II is a member of the group of phenol, o-cresol and anisole.

7. A process according to any one of the preceding claims, wherein the solvent is methylene chloride.

* * * * *